(12) United States Patent
Kim et al.

(10) Patent No.: US 7,771,117 B2
(45) Date of Patent: Aug. 10, 2010

(54) X-RAY SYSTEM FOR DENTAL DIAGNOSIS AND ORAL CANCER THERAPY BASED ON NANO-MATERIAL AND METHOD THEREOF

(75) Inventors: Jong Uk Kim, Seoul (KR); Hae Young Choi, Ansan-si (KR)

(73) Assignee: Korea Electrotechnology Research Institute, Gyeongsangnam-Do (KR)

( * ) Notice: Subject to any disclaimer, the term of this patent is extended or adjusted under 35 U.S.C. 154(b) by 91 days.

(21) Appl. No.: 12/181,791

(22) Filed: Jul. 29, 2008

(65) Prior Publication Data

US 2009/0310742 A1    Dec. 17, 2009

(30) Foreign Application Priority Data

Jun. 13, 2008    (KR)    ............... 10-2008-0055589

(51) Int. Cl.
  *H05G 1/02*    (2006.01)
  *H01J 35/00*    (2006.01)
(52) U.S. Cl. ............... 378/198; 378/65; 378/121; 378/122
(58) Field of Classification Search ............... 378/119, 378/121, 122, 64, 65, 198
  See application file for complete search history.

(56) References Cited

U.S. PATENT DOCUMENTS

| 5,854,822 | A * | 12/1998 | Chornenky et al. | 378/122 |
|---|---|---|---|---|
| 6,108,402 | A * | 8/2000 | Chornenky | 378/119 |
| 6,148,061 | A * | 11/2000 | Shefer et al. | 378/121 |
| 6,289,079 | B1 * | 9/2001 | Chornenky et al. | 378/143 |
| 6,319,188 | B1 * | 11/2001 | Lovoi | 600/3 |
| 6,324,257 | B1 * | 11/2001 | Halavee | 378/121 |
| 6,415,016 | B1 * | 7/2002 | Chornenky et al. | 378/122 |
| 6,438,206 | B1 * | 8/2002 | Shinar et al. | 378/123 |
| 6,477,233 | B1 * | 11/2002 | Ribbing et al. | 378/136 |
| 6,487,272 | B1 * | 11/2002 | Kutsuzawa | 378/140 |
| 6,553,096 | B1 * | 4/2003 | Zhou et al. | 378/122 |
| 6,580,940 | B2 * | 6/2003 | Gutman | 600/427 |
| 6,623,418 | B2 * | 9/2003 | Smith | 600/3 |
| 6,661,875 | B2 * | 12/2003 | Greenwald et al. | 378/119 |
| 6,718,012 | B2 * | 4/2004 | Ein-Gal | 378/121 |
| 6,721,392 | B1 * | 4/2004 | Dinsmore | 378/65 |
| 6,771,737 | B2 * | 8/2004 | Kerslick et al. | 378/122 |
| 6,799,075 | B1 * | 9/2004 | Chornenky et al. | 607/117 |
| 6,987,835 | B2 * | 1/2006 | Lovoi | 378/136 |
| 2009/0185660 | A1 * | 7/2009 | Zou et al. | 378/122 |

* cited by examiner

*Primary Examiner*—Allen C. Ho
(74) *Attorney, Agent, or Firm*—The Webb Law Firm

(57) ABSTRACT

A medical X-ray tube system for dental diagnosis and oral cancer therapy based on nano-material is disclosed. The medical X-ray tube system may include a body and an X-ray emission module emitting X-rays using a cathode having a chipped nano-structured material. The X-ray emission module may be separable from the body. The medical X-ray tube system may be formed as a pen that can be inserted in the oral cavity for displaying an accurate image of an inner location of the oral cavity needing a diagnosis. For treatment of oral cancer requiring an appropriate amount of radiation therapy, brachytherapy may be conducted without concern of exposure of normal tissues to radiation because radiation can be directly irradiated to a diseased part. The X-ray emission module may use a chipped nano-structured material, for example, a carbon nanotube.

12 Claims, 4 Drawing Sheets

X-RAY SYSTEM FOR DENTAL DIAGNOSIS AND ORAL CANCER THERAPY BASED ON NANO-MATERIAL AND METHOD THEREOF

CROSS-REFERENCE TO RELATED APPLICATION

This application claims priority from Korean Patent Application No. 10-2008-0055589, filed on Jun. 13, 2008, in the Korean Intellectual Property Office, the entire disclosure of which is incorporated herein by reference.

BACKGROUND OF THE INVENTION

1. Field of the Invention

The present invention relates to an X-ray tube system and a method thereof. More particularly, the present invention relates to a medical X-ray tube system for a dental diagnosis and an oral cancer therapy and the like based on nano material such as carbon nanotube that is proved to have the most excellent performance as an electron emission source, using a quantum-mechanical field emission principle of emitting electrons, and a method thereof.

2. Description of Related Art

Generally, a system for a dental diagnosis or an oral cancer therapy irradiates a light source toward the outside of the oral cavity of a patient and detects an image projected to the inside of the oral cavity to thereby determine the internal defect of the oral cavity. When a tungsten filament type of an X-ray tube is used as the light source, high electric power is required in a cathode portion in order to induce a desired amount of electron emission through thermal electron emission. Also, since the size of the light source is large, it may cause significant inconvenience for application to the system for the dental diagnosis and the oral cancer therapy. Also, even when using an existing carbon nanotube-based X-ray tube, the size of the light source is relatively large. Therefore, it may also cause inconvenience when inserting the tube in the oral cavity for purpose of the dental diagnosis and the oral cancer therapy.

As described above, in the case of the conventional X-ray system or carbon nanotube-based X-ray tube for the dental diagnosis, the size thereof is large. Therefore, when imaging using an X-ray source described above in the oral cavity for the diagnosis, there is some constraint on an imaging portion. Since it is not readily movable, it is difficult to quickly complete X-ray imaging. Accordingly, there is a need for a medical device that can solve the above inconveniences and obtain an accurate image of a desired local portion.

SUMMARY OF THE INVENTION

An aspect of the present invention provides a medical X-ray tube system for a dental diagnosis and an oral cancer therapy that can significantly reduce the size and weight of an existing X-ray camera and carbon nanotube-based radiation tube and thus can be readily used, and a method thereof.

Another aspect of the present invention also provides a medical X-ray tube system for a dental diagnosis and an oral cancer therapy that can overcome disadvantages such as a lifetime reduction of a carbon nanotube cathode portion and electrical arching by concentrating field in an edge of a substrate in a cathode module of a carbon nanotube-based radiation tube and thereby can overcome unreality of commercialization by a short lifetime of the existing carbon nanotube-based X-ray tube, and a method thereof.

Another aspect of the present invention also provides a medical X-ray tube system for a dental diagnosis and an oral cancer therapy that can enhance the low stability and efficiency of an existing tungsten filament and carbon nanotube-based X-ray tube and can overcome difficulties in obtaining an image of a subject with various sizes and thicknesses due to a limited function of the existing tungsten filament-based dental X-ray camera and thereby can obtain an accurate image of a desired local portion, and a method thereof.

According to an aspect of the present invention, there is provided a medical X-ray tube system including: an X-ray emission module emitting X-rays using a chipped nano-structured material, wherein the X-ray emission module is separable from a body.

In this instance, the X-ray emission module may be rotatable via a rotation axis formed on the body.

Also, the medical X-ray tube system may be manufactured in the form of a pen or a pencil. The X-ray emission module may approach an inner or outer local portion of human body including inside and outside of the oral cavity to thereby emit X-rays to the approached local portion. Also, the X-ray emission module may be used for diagnoses and cancer therapy including a dental diagnosis and an oral cancer therapy.

Also, the medical X-ray tube system may be used as a brachytherapy apparatus that irradiates X-rays to only a cancer cell excluding a normal tissue.

Also, the nano-structured material may include carbon nanotube, carbon nanofiber (CNF), nanowire, graphene, or nanodiamond.

Also, the X-ray emission module may include an electron emission module comprising a grid portion and a cathode fixed by a fixing unit. An electron beam from the cathode may be extracted from the grid portion in a vacuum state.

Also, the vacuum state may be maintained by connecting a pipe in the type of a cable to a vacuum line combined with a hole formed in the X-ray emission module and inhaling the inside air of the X-ray emission module via the pipe.

Also, the X-ray emission module may include: an electron emission module based on the nano-structured material; a focusing lens focusing an electron beam coming from the electron emission module; and an anode portion emitting X-rays by the electron beam from the focusing lens.

Also, the anode portion may include a transmission-type target form of applying tungsten or molybdenum to a beryllium (Be) window.

Also, a power supply and vacuum state of the medical X-ray tube system may be controlled by a computer system. The X-rays emitted from the X-ray emission module and transmitting a diagnostic target may be detected by a detector to thereby display a corresponding image on a display unit interworking with the computer system.

According to another aspect of the present invention, there is provided a diagnostic method of a medical X-ray tube system, the method including: emitting X-rays using a chipped nano-structured material to project the emitted X-rays toward a diagnostic target; and detecting, using a detector, the X-rays transmitting the diagnostic target to display a corresponding image, wherein the X-ray tube system of which an X-ray emission module is separable from a body is used in order to replace a cathode portion that is included in the X-ray emission module and is based on the nano-structured material.

EFFECT OF THE INVENTION

An X-ray tube system and a method thereof according to the present invention may reduce the size and weight of an existing tungsten filament or carbon nanotube-based radiation tube and readily position the radiation tube in a desired location and thereby develop a user-friendly product.

Also, an X-ray tube system and a method thereof according to the present invention may improve the efficiency of tube current according to uniform emission of electron beams from a carbon nanotube cathode portion and may also foster commercialization of a carbon nanotube-based radiation tube according to a long lifetime of the cathode portion.

Also, an X-ray tube system and a method thereof according to the present invention may select a voltage and a current amount according to an imaging portion and may also adjust the voltage and the current amount in a type of a manual and thus significantly solve constraints by the shape of a subject.

Also, an X-ray tube system and a method thereof according to the present invention may overcome the limit of the conventional art regarding the measurement and inspection for minute defect less than or equal to a micro level and may develop an X-ray light source, which is generally dependent on imports, using a highly efficient new technology of our own country, and thereby supply the developed light source to electronic medical instruments at more reasonable prices. Therefore, it is possible to make economical and industrial revenues, and increase the industrial applicability associated with medical diagnoses. Also, by applying the present invention to a brachytherapy apparatus for patients with the oral cancer needing radiation therapy, it is possible to significantly reduce concerns regarding exposure dose of normal tissues, which may occur by directly irradiating the radiation.

BRIEF DESCRIPTION OF THE DRAWINGS

The above and other aspects of the present invention will become apparent and more readily appreciated from the following detailed description of certain exemplary embodiments of the invention, taken in conjunction with the accompanying drawings of which.

DETAILED DESCRIPTION OF EXEMPLARY EMBODIMENTS

Figure 1:
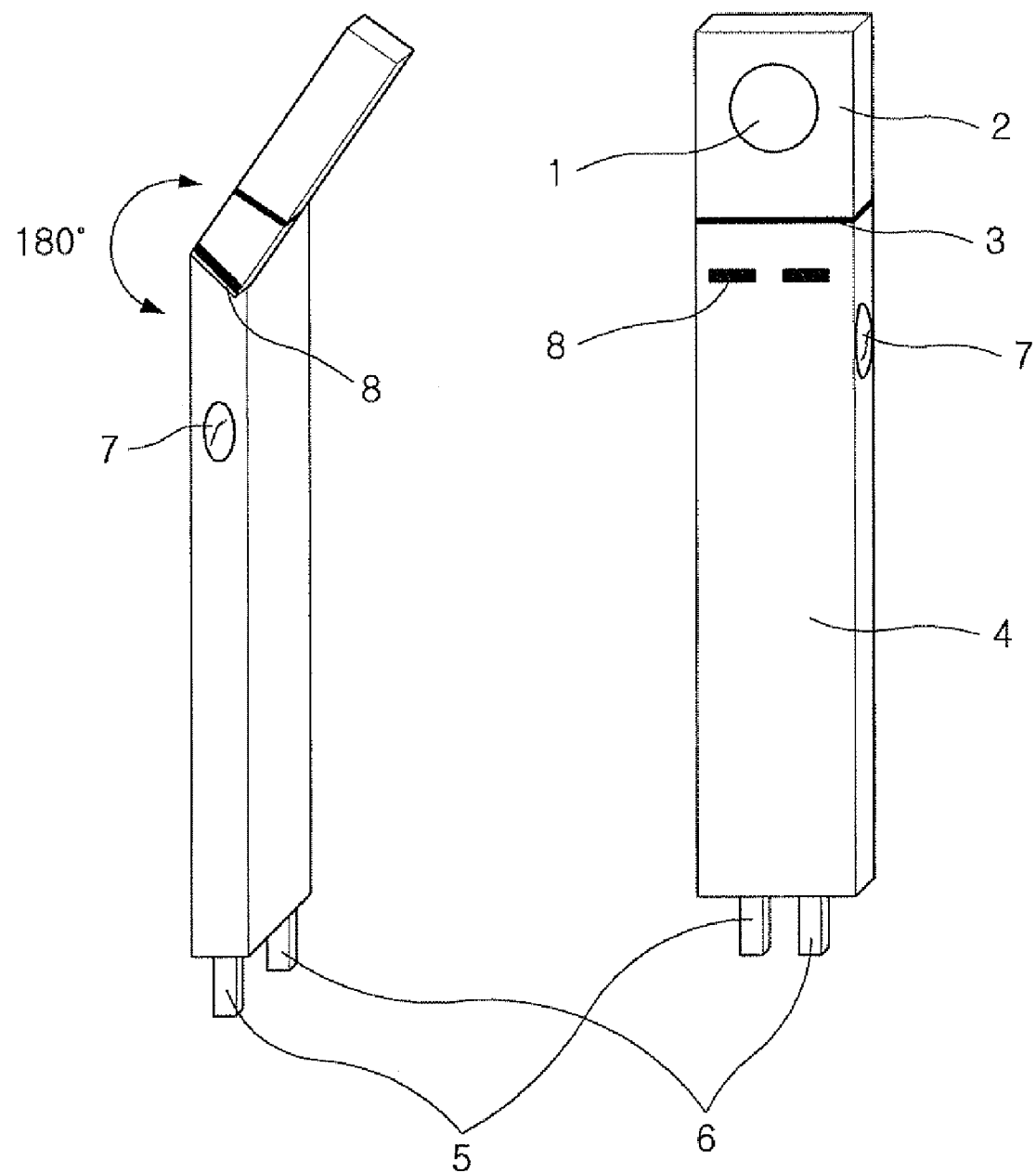
FIG. 1 is a diagram illustrating a rotatable carbon nanotube-based X-ray tube system in the form of a pen according to an embodiment of the present invention.

Reference will now be made in detail to exemplary embodiments of the present invention, examples of which are illustrated in the accompanying drawings, wherein like reference numerals refer to the like elements throughout. The exemplary embodiments are described below in order to explain the present invention by referring to the figures.

FIG. 1 is a diagram illustrating a rotatable carbon nanotube-based X-ray tube system in the form of a pen according to an embodiment of the present invention.

Figure 2:
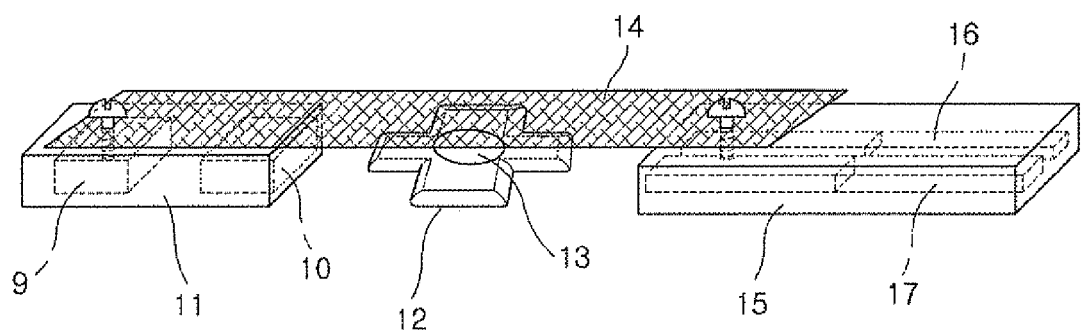
FIG. 2 is a perspective view illustrating a carbon nanotube-based electron emission module according to an embodiment of the present invention.

Referring to FIG. 1, the X-ray tube system according to an embodiment of the present invention includes an X-ray emission module 2 including an X-ray emission window 1, an X-ray emission module separator 3, an X-ray emission system body 4, a feed-through 5 for applying voltage to a carbon nanotube cathode portion 12 of FIG. 2 and a grid portion 14 of FIG. 2, a cable 6 for generating high voltage and a vacuum atmosphere in the system, a grid portion power supply switch 7 for extracting electrons from the carbon nanotube cathode emitter 13, which is located on top of the carbon nanotube cathode portion 12, and a rotation axis 8 of the X-ray emission module 2.

As shown in FIG. 1, the dental X-ray tube system in the form of the pen according to an embodiment of the present invention is constructed to be easily separated from and assembled to the X-ray emission module 2 using the X-ray emission module separator 3, by considering that a cathode portion of the X-ray emission module 2 to include an electron emission device needs to be replaced after a predetermined period of time due to its short lifetime. As described above, the dental X-ray tube system is in a small and convenient structure such as a pen or a pencil to emit X-rays and thus can be easily inserted in the oral cavity to take and obtain an image. Specifically, the dental X-ray tube system may be readily used for the dental diagnosis in the form of inserting the dental X-ray tube system into a portion of the oral cavity needing a diagnosis, rotating the system using the rotation axis 8, and irradiating X-rays through manipulation of the switch 7 to detect an image via an externally installed X-ray detector (not shown). For the oral cancer therapy, the dental X-ray tube system may be directly approached to a diseased portion inside of the oral cavity to irradiate an appropriate amount of radiation. Therefore, the dental X-ray tube system may be applicable in various types of medical systems such as a brachytherapy system that can project radiation only to cancer cells without exposure dose of normal tissues.

Also, carbon nanotube corresponding to the electron emission device in the X-ray emission module 2 may be chipped and thus the size thereof may be standardized and be made in small size. A user-friendly utilization environment is enabled through a simple button manipulation using a simple program interworking with an external measurement system.

Also, while constantly maintaining a vacuum level in the X-ray emission module 2 through connection to a predetermined vacuum pump at all times, a carbon nanotube-based high quality X-ray may be generated. Therefore, the dental X-ray tube system may be usefully employed for the dental diagnosis and the oral cancer therapy, or for other disease diagnoses and cancer therapies, with a low dose.

Hereinafter, an X-ray tube system according to an embodiment of the present invention will be further described in detail with reference to FIGS. 2 through 4.

FIG. 2 is a perspective view illustrating a carbon nanotube-based electron emission module according to an embodiment of the present invention.

Referring to FIG. 2, the electron emission module installed in the X-ray emission module 2 includes a holder 11 including a fixing holder 9 and a hole 10, the cathode portion 12 with chipped carbon nanotube, a carbon nanotube cathode 13 for electron emission, a grid portion 14 for extracting electrons from the cathode 13, and a fixing holder and power supply line module 15. The fixing holder and power supply line module 15 includes a holder and power supply line 16 for fixing a right portion of the grid portion 14 and supplying the power thereto, and another holder and power supply line 17 for fixing a right portion of the cathode portion 12 and supplying the power thereto.

The left and right of the grid portion 14 may be fixed using the fixing holder 9 and the holder and power supply line 16. In this instance, it is possible to fix the grid portion 14 by forming a predetermined hole in the fixing holder 9 and the holder and power supply line 16 and inserting, into the hole, a fixing unit made of a bolting material. The cathode portion 12 may be fixed by inserting the left wing of the cathode portion 12 into the hole 10 and inserting the right wing of the cathode portion 12 into the holder and power supply line 17. The grid portion 14 may be supplied with the power via the holder and power supply line 16. The cathode portion 12 may be supplied with the power via the holder and power supply line 17.

Prior to growing a carbon nanotube field emission source to be used as the cathode 13 for electron emission, corners of a metal plate with the sharpened edge may be grinded.

When manufacturing a carbon nanotube cathode according to a screen printing scheme, an appropriate amount of carbon nanotubes may be applied on a metal plate by spraying carbon nanotube powders over the whole surface of the conductive metal plate twice or three times using a spray gun.

Also, when manufacturing the carbon nanotube cathode according to a chemical vapor deposition (CVD) scheme, it is possible to grow carbon nanotubes by applying a buffer layer such as TiN on the metal plate with the grinded corners, applying a catalyst such as Ni or Fe on the buffer layer, forming seed particles through an etching process using argon or helium gas, and then injecting carbon nanotube source gas such as $C_2H_2$.

When growing carbon nanotubes corresponding to the field emission source on the plate, it is possible to form a cathode by applying carbon nanotubes only on a central portion excluding edges of the plate.

The carbon nanotube is in the form of a tube where hexagonal crystal lattices consisting of six carbons are connected to each other. Since the diameter of the tube is only some to tens of nanometers, the tube is called "carbon nanotube". The diameter of carbon nanotube is a nanometer size and the length of carbon nanotube can grow from tens of nanometers to tens of micrometers. Therefore, field enhancement factor $\beta$ that is a parameter to determine the field emission capability of electron is greater than or equal to 1000, which is larger than other materials. Consequently, in comparison to the existing scheme of extracting electrons from the tungsten filament using thermal electron emission, it is possible to more readily emit electrons. Since the quantum-mechanical field emission scheme is used for extracting the same amount of electrons, a relatively small amount of power may be consumed in comparison to the thermal electron emission scheme.

As described above, the X-ray emission module 2 is manufactured based on carbon nanotube that is currently in the spotlight as the electron emission device. The manufactured X-ray emission module 2 is installed to the dental X-ray tube system and is used. Therefore, in comparison to the existing tungsten filament-typed X-ray tube system, the carbon nanotube-based X-ray tube system according to the present invention may consume a small amount of power and have high resolution. Accordingly, the X-ray tube system according to the present invention may be applicable to various types of highly efficient radiation tube systems, for example, X-ray tube systems, for diagnoses and cancer therapies such as a dental diagnosis and oral cancer therapy.

Although carbon nanotube has been described as a nanostructured material, the present invention is not limited thereto. In addition to the carbon nanotube, it is possible to use the nano-structured material with the excellent electron emission efficiency such as carbon nanofiber (CNF), nanowire, graphene, nanodiamond, and the like.

Figure 3:
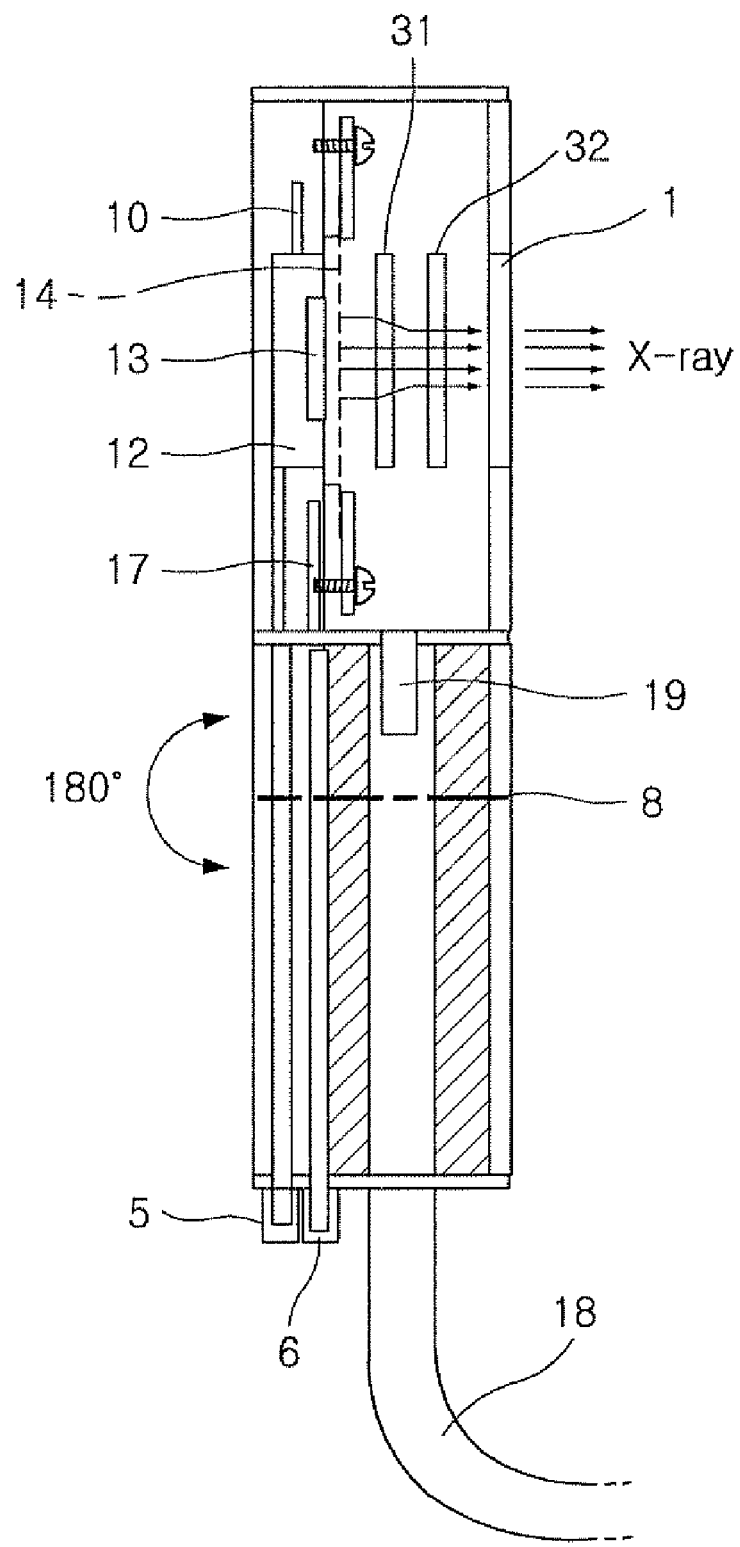
FIG. 3 is a cross-sectional view illustrating an X-ray tube system mounted with an electron emission module according to an embodiment of the present invention.

FIG. 3 is a cross-sectional view illustrating an X-ray tube system mounted with the electron emission module of FIG. 2 according to an embodiment of the present invention.

As shown in FIG. 1, the X-ray emission module 2 with the electron emission module of FIG. 2 may be provided in an upper portion of the body of the X-ray tube system. A pipe 18 in the form of a cable may pass through inside of the X-ray tube system body to be connected to a vacuum line 19. The vacuum line 19 may be combined with a corresponding hole of the X-ray emission module 2. Accordingly, the vacuum atmosphere may be maintained by connecting a vacuum pump to the pipe 18 to operate the vacuum pump and inhaling the inside air of the X-ray emission module 2.

When electrons are emitted via a cathode 13 of the electron emission module in the vacuum atmosphere, electrons coming via a grid portion 14 may be focused on a focusing lens 31, which will be a single or double focusing type of lens, to generate X-rays in an anode portion 32. Specifically, electrons may be generated in the carbon nanotube due to voltage applied to the cathode 13 and the grid portion 14. While the generated electrons are being focused by the focusing lens 31, the electrons may collide with the anode portion 32 installed for X-ray generation to thereby generate X-rays at the same time.

The electron emission module in the X-ray tube system is constructed as a chip and is connected with the pipe 18 for the vacuum atmosphere, whereby the vacuum atmosphere is sufficiently formed in the X-ray tube system, enabling electron generation via field emission. The anode portion 32 may be in the form of a transmission-type target form of applying, to a beryllium (Be) window, a material with excellent X-ray generation efficiency such as tungsten and molybdenum. When electron beams collide with the anode portion 32, X-rays may transmit an anode target and be externally emitted. When the electron beams are focused by the focusing lens 31 disposed between the grid portion 14 and the anode portion 32, the anode portion 32 may emit high resolution X-rays of idealistic point light source less than or equal to tens of micrometers. The above structure may be applicable to an X-ray microscope.

Figure 4:
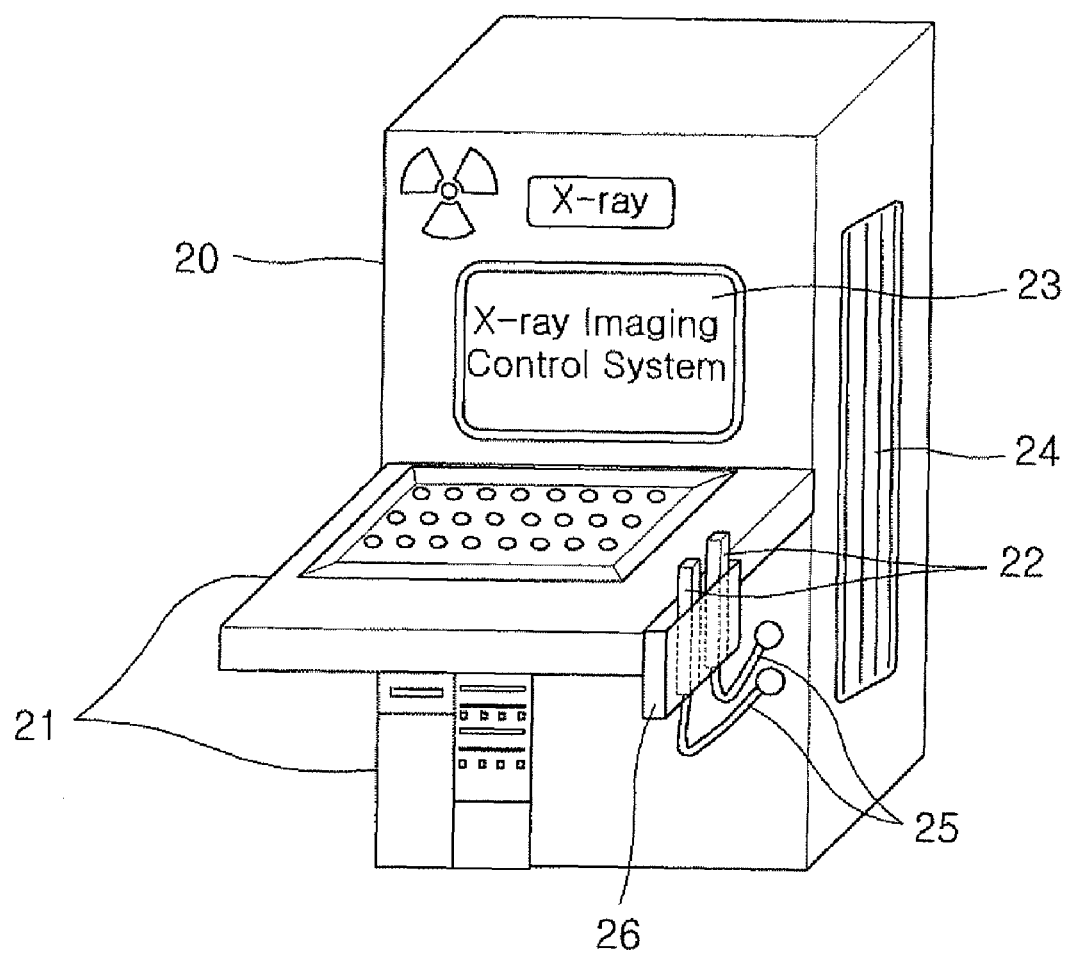
FIG. 4 is a perspective view illustrating a dental X-ray imaging system based on carbon nanotube according to an embodiment of the present invention.

FIG. 4 is a perspective view illustrating a dental X-ray imaging system based on carbon nanotube according to an embodiment of the present invention.

Referring to FIG. 4, the X-ray imaging system includes a body 20 for embedding a power supply device, a vacuum pump, and the like, a computer system 21 for obtaining an image, a portable radiation tube 22 for a dental diagnosis, an image display monitor 23, a cooling fan device 24, a cable-type pipe 25 for forming the vacuum atmosphere and a cable for supplying power to the X-ray tube system, and an X-ray tube reception device 26 for arranging and receiving the X-ray tube system. The portable radiation tube 22 may include an X-ray tube system in the structure described above with reference to FIGS. 1 to 3 and an X-ray detector detecting X-rays that are emitted from the X-ray tube system to come out via the oral tissues.

The portable radiation tube 22 may be operated together with a predetermined application program of the computer system 21. For example, predetermined software or hardware installed in the computer system 21 may control the computer system 21 to maintain the electric power or a vacuum level required for the portable radiation tube 22. An oral diagnosis process may be simply performed by inserting the X-ray tube system of FIG. 1 in a portion needing the oral diagnosis, irradiating X-rays toward the portion through manipulation of the switch 7 while rotating the X-ray tube system via the rotation axis 8, and detecting an image in outside of the oral cavity via the X-ray detector. According to control of the computer system 21, the detected image may be stored in a predetermined memory and be displayed on the image display monitor 23.

A radiation imaging system for the dental diagnosis and the like, used as above, may approach a local portion in the oral cavity that was difficult to measure in the existing portable radiation system, and thereby obtain an image of the local portion. In particular, the radiation imaging system is designed so that dentists may conveniently and readily use the system. Thus, the radiation imaging system is expected to bring great help in related medical fields. Also, since the size of the system is not large, the spatial applicability may be improved. In this aspect, the system can be said more applicable. In the case of a currently commercialized X-ray camera for the dental diagnosis, the X-ray camera may be convenient for its use to some extent, whereas it weights about 2 kg. Therefore, when a user takes an X-ray, shaking exists, which makes an image indistinct. Because of this, the utility of the X-ray camera is low. Accordingly, the radiation system proposed in the present invention is in the form of a pen or a pencil and thus it is possible to significantly reduce the weight. When the radiation system is commercialized, it is expected to bring many benefits in related fields.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. An oral X-ray tube system comprising:
   a hand-held body having a pen-shape;
   an X-ray emission module emitting X-rays using a cathode comprising a chipped nano-structured material,
   wherein the X-ray emission module is separable from the body.

2. The system of claim 1, wherein the X-ray emission module is rotatable relative to the body.

3. The system of claim 1, wherein:
   the medical X-ray tube system enables the X-ray emission module to approach an inner or outer local portion of the human body including inside and outside of the oral cavity and to emit X-rays to the approached local portion for diagnoses and cancer therapy including a dental diagnosis and an oral cancer therapy.

4. The system of claim 1, wherein the nano-structured material comprises carbon nanotube, carbon nanofiber (CNF), nanowire, graphene, or nanodiamond.

5. The system of claim 1, wherein:
   the X-ray emission module comprises an electron emission module comprising a grid portion and the cathode, and further comprises a vacuum line such that an electron beam from the cathode is extracted from the grid portion in a vacuum state.

6. The system of claim 5, further comprising a pipe, wherein the vacuum state is established by the pipe connected to the vacuum line combined with a hole formed in the X-ray emission module and evacuating the inside air of the X-ray emission module via the pipe.

7. The system of claim 6, wherein the pipe is in the form of a cable.

8. The system of claim 1, wherein the X-ray emission module comprises:
   an electron emission module comprising a grid portion and the cathode;
   a focusing lens focusing an electron beam coming from the electron emission module; and
   an anode portion emitting X-rays as a result of the electron beam from the focusing lens.

9. The system of claim 8, wherein the anode portion includes a transmission-type target form of applying tungsten or molybdenum to a beryllium (Be) window.

10. A diagnostic method using an oral X-ray tube system, the method comprising:
    emitting X-rays using a chipped nano-structured material:
    projecting the emitted X-rays toward a diagnostic target; and
    detecting the X-rays transmitted through the diagnostic target to display a corresponding image,
    wherein the X-ray tube system comprises a hand-held body having a pen-shape and an X-ray emission module separable from the body, the X-ray emission module comprising a replaceable cathode comprising the nano-structured material.

11. The method of claim 10, wherein:
    a power supply and vacuum state of the oral X-ray tube system is controlled by a computer system, and the X-rays transmitted through the diagnostic target are detected to display the corresponding image on a display unit interworking with the computer system.

12. The method of claim 10, wherein the oral X-ray tube system is used as a brachytherapy apparatus that irradiates X-rays to only cancer cells excluding normal tissue.

* * * * *